United States Patent [19]

Thompson

[11] 4,424,165
[45] Jan. 3, 1984

[54] VOLATILE CERIUM COMPLEXES

[75] Inventor: David A. Thompson, Horseheads, N.Y.

[73] Assignee: Corning Glass Works, Corning, N.Y.

[21] Appl. No.: 418,216

[22] Filed: Sep. 15, 1982

[51] Int. Cl.³ ............................................. C07F 5/00
[52] U.S. Cl. ................................................ 260/429.2
[58] Field of Search ..................................... 260/429.2

[56] References Cited

U.S. PATENT DOCUMENTS

| | | | |
|---|---|---|---|
| 4,176,918 | 12/1979 | Labes | 252/299.1 X |
| 4,201,721 | 5/1980 | Hallgren | 528/219 X |
| 4,206,132 | 6/1980 | Sievers | 260/429.2 |

Primary Examiner—Leland A. Sebastian
Attorney, Agent, or Firm—van der Sterre K.

[57] ABSTRACT

A volatile and thermally stable complex of cerium, Cd(fod)$_4$, and alkali metal-cerium $\beta$-diketonate intermediates useful in its preparation and as sources of mixed metals, such as Na[Ce(fod)$_4$], are described.

3 Claims, 3 Drawing Figures

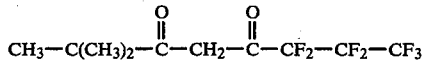

VOLATILE CERIUM COMPLEXES

BACKGROUND OF THE INVENTION

The present invention relates to organometallic compounds and particularly to a β-diketonate complex of cerium which exhibits unusually high volatility and stability.

Volatile metal complexes are of interest for a variety of applications, including use as fuel additives, metal vapor sources for vapor phase reactions, and gas transport reagents. A useful discussion of β-diketonate complexes and their uses is provided by R. E. Sievers et al. in *Science*, 201 [5352], pages 217–223 (July 1978), wherein numerous references to the preparation and use of these complexes are cited.

β-diketonates of the rare earth or lanthanide series of elements of the Periodic Table have the general formula Ln(AA')$_3$, wherein Ln is the metal element and AA' represents the diketonate ligand which forms the complex. Discussions of the synthesis and properties of the rare earth β-diketonate complexes usually do not treat the cerium complexes. This is due to the complexity arising because cerium has two stable oxidation states.

The trivalent paramagnetic complexes of Ce$^{III}$ with β-diketones such as acetylacetone [Ce(acac)$_3$], trifluoroacetylacetone [Ce(tfa)$_3$], and hexafluoroacetylacetone [Ce(hfa)$_3$] are frequently mentioned but only a few tetravalent (Ce$^{IV}$) compounds have been reported. These include Ce(acac)$_4$, Ce(tfa)$_4$ and complexes of cerium with 2,2,6,6-tetramethyl-3,5-heptanedione(thd) and the aromatic diketone (C$_6$H$_5$CO)$_2$CH, the first two being made by the oxidative decomposition of trivalent complexes incorporating the same ligands in an inert solvent in flowing air or oxygen. In the case of Ce(tfa)$_4$, yields arepoor even in the presence of excess quantities of the free β-diketone (Htfa).

Cerium complexes have also been formed with some of the 8-carbon β-diketones, including 6,6,7,7,8,8,8-heptafluoro-2,2-dimethyl-3,5-octanedione [Ce(fod)$_3$] and 2,2,7-trimethyl-3,5-octanedione [Ce(tod)$_4$]. However, none of these cerium complexes have exhibited sufficient stability and volatility to be truly useful as a cerium metal vapor source for vapor phase reactions designed to produce cerium-containing products.

It is therefore a principle object of the present invention to provide a cerium complex and a precursor useful in the production of that complex, which result in a stable compound exhibiting sufficient volatility for use as a vapor source of cerium.

Other objects and advantages of the invention will become apparent from the following description.

SUMMARY OF THE INVENTION

The present invention provides a Ce$^{+4}$ β-diketonate complex of improved stability and volatility, as well as a group of volatile Ce$^{+3}$ β-diketonate complexes useful as intermediates in the production of the pure Ce$^{+4}$ complex and as volatile sources for mixtures of cerium and alkali metals.

The complexes of the invention are complexes of cerium with the fluorinated β-diketone 6,6,7,7,8,8,8-heptafluoro-2,2-dimethyl-3,5-octanedione (Hfod), a β-diketone having the molecular structure:

$$CH_3-C(CH_3)_2-\overset{O}{\underset{\|}{C}}-CH_2-\overset{O}{\underset{\|}{C}}-CF_2-CF_2-CF_3$$

Cerium β-diketonate complexes of this β-diketone are produced by the deprotonation of the diketone at the C4 position to produce (fod)$^-$ anions or ligands. Four of these ligands then combine with a cerium ion to form a complex wherein the metal is in 8-fold coordination with the oxygen atoms in the ligands. The formula of the Ce$^{+4}$ complex with this β-diketone is Ce(fod)$_4$. The formula of the Ce$^{+3}$ complexes, which can be characterized as alkali metal β-diketonate salts, is M[Ce(fod)$_4$] wherein M is an alkali metal selected from the group Li, Na, K, Rb and Cs. These salts can be used to produce pure Ce(fod)$_4$ by a process of oxidation, or they can be used as sources for Ce-M mixtures in vapor deposition reactions to form metal or oxide products.

Ce(fod)$_4$ offers significant advantages over prior art β-diketonate complexes of cerium with respect to both thermal stability and volatility. It has a vapor pressure at least 2 orders of magnitude higher than that of the 3-complex with the same ligand, Ce(fod)$_3$. Also, it is stable against decomposition at temperatures sufficiently high to permit vapors of the compound to be efficiently generated at substantial partial pressures. Thus the compound is believed to be superior to previous cerium compounds when used, for example, as a vapor source of cerium in a chemical vapor deposition reaction.

BRIEF DESCRIPTION OF THE DRAWING

The invention may be further understood by reference to the drawings wherein.

DETAILED DESCRIPTION

The preparation of pure cerium (fod) complexes in accordance with the invention involves the deprotonation of the β-diketone in the presence of cerium (III) nitrate. The following example describes a suitable method for preparing such a complex.

EXAMPLE 1

A 68.2 g sample of the β-diketone 6,6,7,7,8,8,8-heptafluoro-2,2-dimethyl-3,5-octanedione (hfod) is added to 115 ml of 2 M aqueous NH$_4$OH resulting in a white precipitate which is separated and dissolved in a mixture of 200 ml of water and 200 ml of methanol. The resulting solution is placed in an addition funnel and is added dropwise to a nitric acid solution of cerium nitrate, the latter solution being made by adding 25.0 g Ce(NO)$_3$.6H$_2$O to 60 ml of 1.4 M HNO$_3$. After addition of the water-methanol solution, 2 M NH$_4$OH is added to the reaction mixture to achieve and maintain a pH of 6.

The resulting mixture separates into a red oil phase and an aqueous phase. The phases are stirred together under oxygen at room temperature to obtain complete oxidation of Ce$^{+3}$ to Ce$^{+4}$. This can be accomplished within about 24 hours. Thereafter, hexanes (200 ml) are added and the hexane layer containing the product is separated from the aqueous phase, filtered, and evaporated to dryness in a rotary evaporator.

The red solid is redissolved in 300 ml of hexanes and 600 ml of ethanol is added. Crystals of red Ce(fod)$_4$ form after cooling of the solution.

Figure 1:
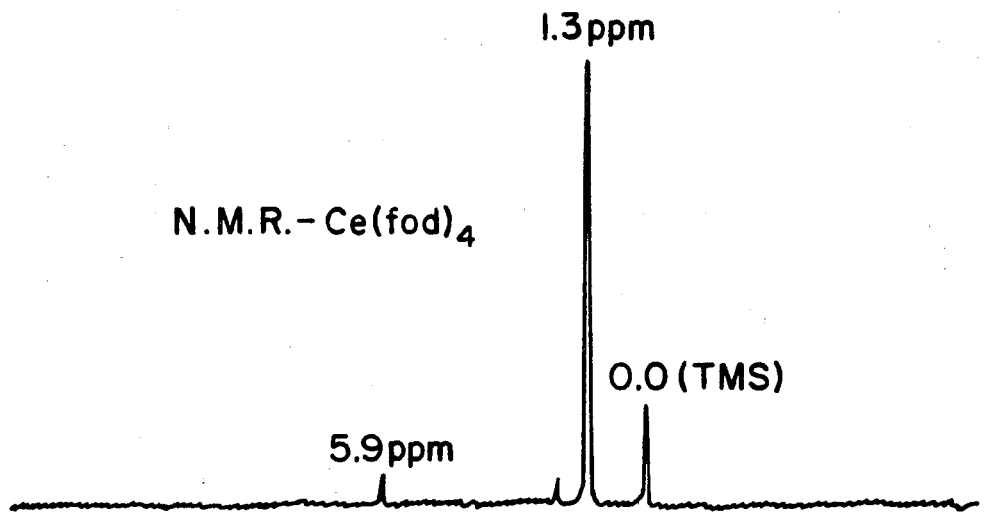
FIG. 1 contains a proton nuclear magnetic resonance spectrum for the β-diketonate complex Ce(fod)$_4$.

Proton nuclear magnetic resonance and magnetic susceptibility measurement of the product indicates that the yield is substantially entirely Ce(fod)$_4$, with no evidence of Ce(fod)$^-_4$. FIG. 1 of the drawing shows a proton nuclear magnetic resonance spectrum of this product in a CCl$_4$ solvent against a tetramethylsilane standard at 60 MHz, from which the absence of trivalent cerium compounds of (fod) can be inferred.

In an alternative preparation procedure, Ce(fod)$_4$ is produced by the oxidation of the intermediate Na[Ce(fod)$_4$]. This intermediate results when the deprotonation of the β-diketone is carried out with NaOH. An illustrative procedure is set out in the following example.

EXAMPLE 2

A methanol solution of cerium nitrate is prepared by adding 110 g of Ce(NO$_3$)$_3$.6H$_2$O to 250 ml of methanol. A methanol solution of Hfod is then prepared by adding 300 g of the β-diketone to 250 ml of methanol in an addition funnel. This latter solution is then added to the cerium nitrate solution with continuous stirring.

After this addition has been completed, 4 M NaOH is added to the mixture dropwise with pH monitoring until a pH of 7-8 is attained. 600 ml of water and 500 ml of hexanes are then added to the reaction mixture, and a separation of layers occurs with concentration of the β-diketonate product in the hexane layer.

The hexane layer is separated and rotary-evaporated to dryness. The product is a crystalline mixture of Na[Ce(fod)$_4$] and Ce(fod)$_4$, with the proportion of the latter compound depending upon the extent of oxidation which has been permitted to occur after adding NaOH. Separation of the Ce(fod)$_4$ from the Na[Ce(fod)$_4$] can be effected by dissolving the product in hexane and separating the Na[Ce(fod)$_4$] from the solution by adding ethanol, in which the solubility of the sodium complex is relatively high.

Oxidation of Na[Ce(fod)$_4$] to Ce(fod)$_4$

To convert the sodium complex to Ce(fod)$_4$, a 255 g sample of Na[Ce(fod)$_4$] is dissolved in 500 ml of hexanes and 500 ml of distilled water. This mixture is then refluxed at low temperature for about 60 hours while bubbling pure O$_2$ gas through the liquid. At the solution of this oxidation treatment, the solution is deep red in color, with a tan solid present on the sides of the reaction container.

The solution is separated, filtered, and rotary-evaporated to dryness, the product consisting predominantly of Ce(fod)$_4$ with some residual Na[Ce(fod)$_4$] which is separated from the pure cerium product by partitioning in an ethanol/hexane mixture. The tan solid recovered from the oxidation step is identified by x-ray diffraction as CeO$_2$.

The β-diketonate products produced in accordance with Example 2 above are examined by differential scanning calorimetry to determine melting points. The results are set forth in Table I below.

TABLE I

| DSC ENDOTHERMIC PEAKS | | |
|---|---|---|
| Compound | Major | Minor |
| Ce(fod)$_4$ | 97° C. | 84° C., 156° C. |
| Na[Ce(fod)$_4$] | 120° C. | 65° C. |

The infrared spectra of the two complexes are similar over the region from 4,000 to 400 cm$^{-1}$, but exhibit important differences in the C=O region, due to the difference in the oxidation state of cerium. The C=O (C=C) stretch frequencies are expected to shift to lower regions as the oxidation state of the metal increases. For Na[Ce(fod)$_4$], these stretching frequencies are evidenced by a strong peak at 1630 cm$^{-1}$ with a weak shoulder at 1645 cm$^{-1}$. For Ce(fod)$_4$, strong peaks are observed at 1595 cm$^{-1}$ and 1610 cm$^{-1}$.

The preparation of other alkali metal salts of the formula M[Ce(fod)$_4$] would follow that described in Example 2 above, but replacing NaOH with a base such as LiOH or KOH in the deprotonation step. In this way salts such as Li[Ce(fod)$_4$] and K[Ce(fod)$_4$] may be prepared which could be converted to Ce(fod)$_4$ or used directly as sources of metal mixtures.

The very low melting point of Ce(fod)$_4$, e.g., about 97° C., is a particular advantage where the compound is to be used to supply cerium-containing vapors for a vapor phase reaction. Both Ce(tod)$_4$ and Ce(tfa)$_3$ exhibit significantly higher melting points, eg., 134° C. and 176° C., respectively.

Figure 2:
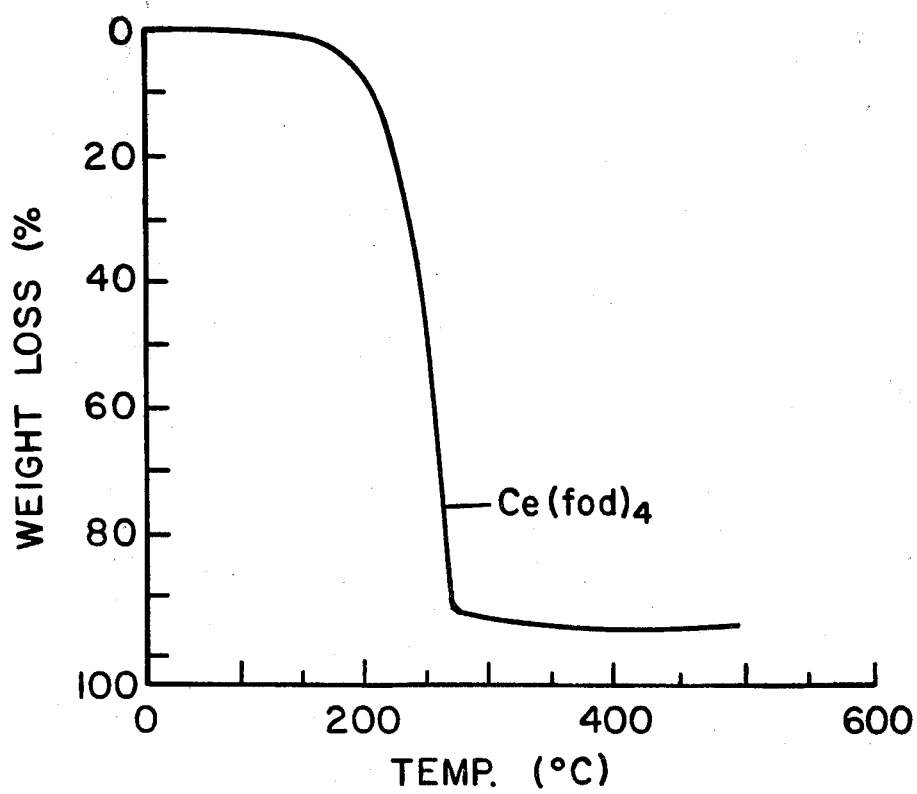
FIG. 2 contains a thermogravimetric analysis curve demonstrating the volatility of Ce(fod)$_4$.

The high volatility and stability of the Ce(fod)$_4$ complex when compared with other trivalent and tetravalent cerium β-diketonates are particularly important. FIG. 2 of the drawing sets forth a thermogravimetric analysis curve for Ce(fod)$_4$ which suggests rapid and complete volatilization of the compound with no evidence of decomposition at temperatures below 275° C. The temperature of 50% volatilization of the sample (T$_{\frac{1}{2}}$), a useful relative measure of volatility, is about 250° C., and no unusual weight fluctuations evidencing thermal decomposition during the course of vaporization are evident.

This volatilization behavior is substantially better than that exhibited by any of Ce(tod)$_4$, Ce(hfa)$_3$ or Ce(tfa)$_3$. Ce(tod)$_4$ exhibits no evidence of decomposition, but has a T$_{\frac{1}{2}}$ temperature of about 320° C., while both Ce(tfa)$_3$ and Ce(hfa)$_3$ exhibit evidence of significant thermal decomposition at these volatilization temperatures during TGA analysis.

Figure 3:
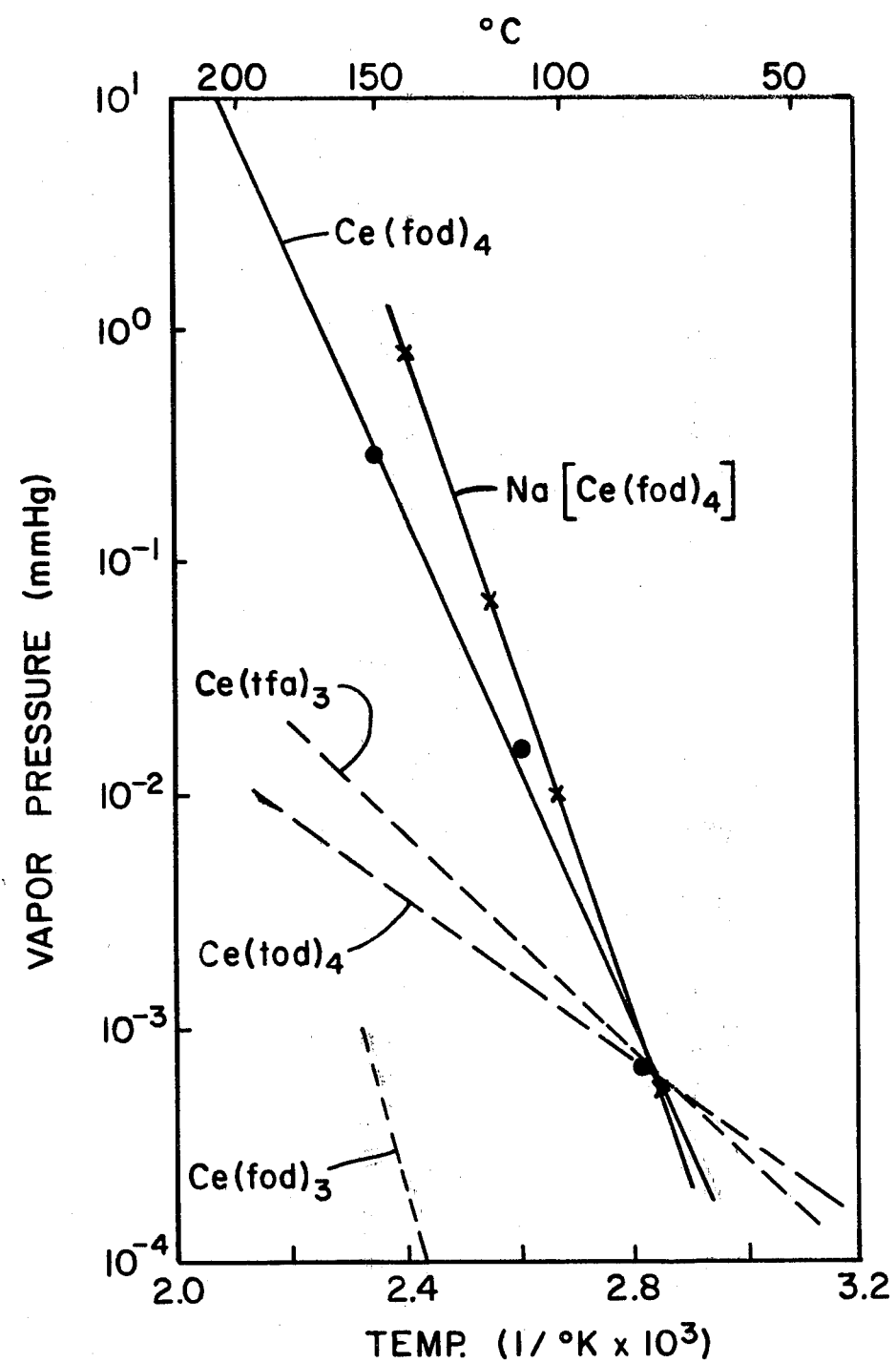
FIG. 3 compares the vapor pressures of Ce(fod)$_4$ and Na[Ce(fod)$_4$] with selected prior art β-diketonate complexes.

The high vapor pressure of the tetravalent cerium (fod) complex also favors its use as a source of cerium vapors for vapor phase reactions. FIG. 3 of the drawing plots vapor pressure as a function of temperature for the cerium β-diketonate complexes Ce(fod)$_4$, Na[Ce(fod)$_4$], Ce(fod)$_3$, Ce(tfa)$_3$, and Ce(tod)$_4$. The data for the complex Ce(fod)$_3$ as taken from the literature. It is evident from a study of FIG. 3 that the complex Ce(fod)$_4$ exhibits significantly higher vapor pressure than any of the Ce(tod)$_4$, Ce(tfa)$_3$, and Ce(fod)$_3$ complexes, particularly at temperatures above 100° C. where these complexes would be used as vapor sources for cerium metal.

FIG. 3 also demonstrates the very significant vapor pressure of the Na[Ce(fod)$_4$] complex. Although analogous alkali metal salts of other rare earth metal diketonates have shown some volatility, the very high volatility of this complex is surprising, suggesting that it could be used as a source of Ce/Na-containing vapors for vapor deposition applications where such a combination is required. It is expected that the other alkali metal salts of this complex would also have this utility.

Of course the foregoing examples are merely illustrative of the invention, and it will be recognized that numerous variations and modifications of the procedures hereinabove described may be resorted to by those skilled in the art within the scope of the appended claims.

I claim:

1. A cerium $\beta$-diketonate complex of $Ce^{+4}$ with 6,6,7,7,8,8,8-heptafluoro-2,2-dimethyl-3,5,octanedione (hfod) which has the molecular formula: $Ce(fod)_4$.

2. A $\beta$-diketonate complex of $Ce^{+3}$ and $M^{+1}$ with 6,6,7,7,8,8,8-heptafluoro-2,2-dimethyl-3,5-octanedione (hfod), having the molecular formula: $M[Ce(fod)_4]$, wherein M is selected from the group: Na, Li, K, Cs and Rb.

3. A $\beta$-diketonate complex in accordance with claim 2 wherein M is Na.

* * * * *

UNITED STATES PATENT AND TRADEMARK OFFICE
CERTIFICATE OF CORRECTION

PATENT NO. : 4,424,165
DATED : January 3, 1984
INVENTOR(S) : David A. Thompson

It is certified that error appears in the above-identified patent and that said Letters Patent is hereby corrected as shown below:

Column 1, line 15, change "[5352]" to -- [4352] --.

Column 1, line 38, change "arepoor" to -- are poor --.

Column 1, line 41, change "8-carbon" to -- 10-carbon --.

Column 3, line 53, change "solution" to --conclusion--.

Column 6, line 3, change "(hfod)" to -- (Hfod) --.

Column 6, line 6, change "(hfod)' to -- (Hfod) --.

Signed and Sealed this

Fifteenth Day of May 1984

[SEAL]

Attest:

GERALD J. MOSSINGHOFF

Attesting Officer   Commissioner of Patents and Trademarks